United States Patent [19]

Arison et al.

[11] Patent Number: 5,362,752

[45] Date of Patent: Nov. 8, 1994

[54] CHEMICAL COMPOUNDS

[75] Inventors: Byron H. Arison, Watchung; Gregory D. Berger, Belle Mead; Leeyuan Huang, Watchung; John G. MacConnell, Westfield, all of N.J.

[73] Assignee: Merck & Co., Inc., Rahway, N.J.

[21] Appl. No.: 61,518

[22] Filed: May 17, 1993

[51] Int. Cl.⁵ .................. A61K 31/215; C07C 57/03
[52] U.S. Cl. ...................................... 514/533; 549/328; 549/318; 549/305; 549/292; 549/285; 549/271; 549/270; 549/229; 549/228; 554/116
[58] Field of Search ............... 554/116; 549/328, 318, 549/305, 292, 285, 271, 270, 229, 228; 514/533, 473, 467, 465, 463

[56] References Cited

U.S. PATENT DOCUMENTS 4,871,721  10/1989  Biller ..................... 514/102
5,053,425  10/1991  Bartizal et al. ............ 514/452
5,096,923  3/1993   Bergstrom et al. .......... 514/452

OTHER PUBLICATIONS

E. J. Corey et al., J. Am. Chem. Soc., 98, 1291 (1976).
P. Ortiz de Montellano, J. Med. Chem., 20, 243 (1977).

Primary Examiner—Nicky Chan
Attorney, Agent, or Firm—Catherine A. Dolan; Melvin Winokur

[57] ABSTRACT

New cholesterol lowering compounds are formed from the photochemical treatment of zaragozic acid A.

8 Claims, No Drawings

CHEMICAL COMPOUNDS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e., several grams at a time, and they are not very palatable.

MEVACOR® (lovastatin) and ZOCOR® (simvastatin), now commercially available, are members of a group of very active antihypercholesterolemic agents that function by limiting cholesterol biosynthesis by inhibiting the enzyme HMG-CoA reductase.

Squalene synthase is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol, and isopentyl t-RNA.

Previous efforts at inhibiting squalene synthase have employed pyrophosphate or pyrophosphate analog-containing compounds such as those described in P. Ortiz de Montellano et al. *J. Med. Chem.* 20, 243 (1977) and E.J. Corey and R. Volante, *J. Am. Chem. Soc.*, 98, 1291 (1976). S. Biller (U.S. Pat. No. 4,871,721) describes isoprenoid (phosphinylmethyl) phosphonates as inhibitors of squalene synthase.

Recently, certain nonphosphorus containing inhibitors of squalene synthase have been isolated as natural products. The natural product inhibitor known as Zaragozic Acid A and its use as a cholesterol lowering agent and antifungal agent is described in U.S. Pat. Nos. 5,096,923 issued Mar. 17, 1992, and 5,053,425 issued Oct. 1, 1991. These patents disclose preparation of Zaragozic Acid A by an aerobic fermentation procedure employing a fungal culture MF 5453 (ATCC 20986). MF 5453 is an unidentified sterile fungus isolated from a water sample obtained from the Jalon river in Zaragoza, Spain. A need still remains for a more effective squalene synthase inhibitor, i.e., one that provides a greater antihypercholesterlemic effect and exhibits a good safety profile.

The present invention is directed to photochemical reaction products of Zaragozic Acid A.

DETAILED DESCRIPTION OF THE INVENTION

This invention relates to compounds of structural formula

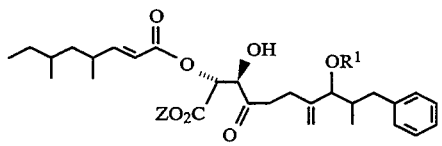

wherein
$R^1$ is selected from the group consisting of hydrogen and acetyl; and
Z is selected from the group consisting of:
(a) hydrogen;
(b) $C_{1-5}$ alkyl;
(c) $C_{1-5}$ alkyl substituted with a member of the group consisting of
  i) phenyl;
  ii) phenyl substituted with methyl, methoxy, halogen (Cl, Br, I, F) or hydroxy; and
  iii) $C_{1-5}$ alkylcarbonyloxy;
(d) —$CH_2$—CH=$CH_2$;

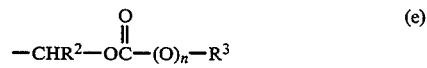

wherein
$R^2$ is —H or $C_{1-4}$alkyl,
n is zero or 1, and
$R^3$ is
  a) $C_{1-5}$alkyl,
  b) phenyl, or
  c) phenyl substituted with X and Y, defined below,
or, when $R^2$ is $C_{1-4}$ alkyl, $R^2$ and $R3$ are joined together to form a monocyclic or bicyclic ring system,
or, $R^3$ is joined together with the carbon to which $R^2$ is attached to form a monocyclic or bicyclic ring system, and $R^2$ represents the bond between $R^3$ and the carbon to which $R^2$ is attached,

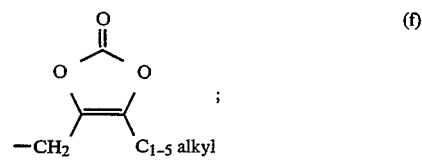

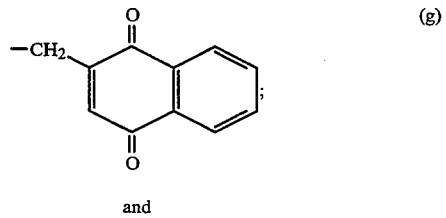

X and Y are each independently selected from:
(1) hydrogen,
(2) hydroxy,
(3) halogen,
(4) trifluoromethyl,
(5) $C_{1-4}$alkyl,
(6) $C_{1-4}$alkyl—O—,
(7) $C_{1-4}$alkyl—C(O)—O—,
(8) —$CO_2C_{1-4}$alkyl,
(10) —$CO_2H$, and
(11) nitro;
or a pharmaceutically acceptable salt thereof.

In one class of the invention is the compound of formula (I) wherein $R^1$ is acetyl and Z is hydrogen or a pharmaceutically acceptable salt thereof. The compound wherein $R^1$ is acetyl and Z is hydrogen is hereafter referred to as Compound A.

In a second class are the compounds of formula (I) wherein $R^1$ is acetyl and Z is $C_1$-$C_5$ alkyl or $C_{1-5}$ alkyl substituted with $C_{1-5}$ alkylcarbonyloxy. In a first subclass are those compounds wherein Z is $C_{1-5}$ alkyl substituted with $C_{1-5}$ alkylcarbonyloxy. Further illustrating this subclass is the compound wherein Z is—CH- 2—O—COC(CH$_3$)$_3$ and hereafter referred to as Compound B. In a second subclass are those compounds wherein Z is C$_{1-5}$ alkyl. Exemplifying this subclass is the compound wherein Z is methyl. This compound is hereafter referred to as Compound C.

Compound A can be formed from Zaragozic Acid A by photochemical treatment of Zaragozic Acid A, under exposure to air, and preferably in the presence of an appropriate catalyst such as Fe$^{3+}$, in a polar aprotic solvent such as DMSO, CH$_3$CN, or DMF. Compound A (wherein R$^1$ is acetate) can be convened to the compound where R$^1$ is H by a biotransformation. A culture of MA 6817 (ATCC 55189) can be employed in this transformation. Alternately, Compound A can be convened to the compound where R$^1$ is H using potassium carbonate in methanol.

The carboxy group of Compound A may be esterified with the appropriate alkylating agent and DBU (1,8-diazabicyclo [5.4.0]undec-7ene).

The present invention is also directed to a method of inhibiting cholesterol biosynthesis which comprises the administration to a subject in need of such treatment a nontoxic therapeutically effective amount of a compound represented by structural formula (I) and pharmaceutically acceptable salts thereof. Specifically, the compounds of this invention are useful as antihypercholesterolemic agents for the treatment of arteriosclerosis, hyperlipidemia, familial hypercholesterolemia and the like diseases. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The present invention is also directed to a method of inhibiting squalene synthase which comprises the administration to a subject in need of such treatment a nontoxic therapeutically effective amount of compound represented by structural formula (I) and pharmaceutically acceptable salts thereof. Specifically, the compounds of this invention are useful in treating disease conditions such as, but not limited to, hypercholesterolemia which result from the action of the enzyme squalene synthase. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorable employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methylglutamine, lysine, arginine, omithine, choline, N,N'-dibenzylethylenediamine, chloroprocaine, diethanolamine, procaine, N-benzylphenethylamine, diethylamine, piperazine, tris(hydroxymethyl)aminomethane, and tetramethylarmnonium hydroxide.

The compounds of this invention may also be administered in combination with other cholesterol lowering agents such as those which inhibit an enzymatic pathway in the biosynthesis of cholesterol. Example of such agents would include but are not limited to HMG-CoA reductase inhibitors, HMG-CoA synthase inhibitors, and squalene epoxidase inhibitors. Illustrative of such inhibitors are lovastatin, simvastatin, pravastatin, and fluvastatin. Other cholesterol lowering agents that may be administered include niacin, probucol, and the fibtic acids, clofibrate and gemfibrozil. Appropriate daily dosages for adults are niacin (2–8 gm), probucol (up to 1000 mg), clofibrate (up to 2 gm) and gemfibrozil (800–1500 mg).

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethyl- aminopropyl)iminotrimethylene dihalide]. The relative amounts of the compounds of this invention and these polymers is between 1:100 and 1:15,000.

The intrinsic squalene synthase inhibitory activity of the compounds of this invention was measured by the standard in vitro protocol described below:

PREPARATION OF HUMAN HEPG2 CELL ENZYME

1. Source: HEPG2 CELL LINE (Liver, hepatoblastoma, Human) ATCC No. HB 8065

2. Cell Growth and Maintenance

Culture Medium: Minimum essential medium (MEM) with non-essential amino acids, sodium pyruvate, and 10% fetal bovine serum. The medium was changed twice weekly. A confluent monolayer was achieved in 1 week. The growth medium is prepared as listed below.

| Solution | Volume (mL) |
| --- | --- |
| 1. MEM (Gibco #320-1090AK) With Earle's salts and L-glutamine | 1000 |
| 2. Penicillin (10,000 units/mL), streptomycin (10,000 mg/mL), Gibco#600-5140 PG | 10 |
| 3. MEM sodium pyruvate, 10 mM (100X) Gibco#320-1140 | 10 |
| 4. MEM nonessential amino acids, 10 mM(100X) Gibco#320-1140AG | 10 |
| 5. L-glutamine, 200 mM (100X), Gibco#320-5030AG | 10 |
| 6. Hyclone fetal bovine serum, defined, Hyclone #A-111-L | 100 |

Subculture Procedure: Remove medium, wash with PBS, add fresh trypsin (0.25%)-EDTA (0.02%) with Hank's Balanced Salt solution and let flask stand for a minute and remove the trypsin solution. Incubate flask at 37° C. until cells detached. Add fresh medium, disperse and dispense cells into new flasks. Subcultivation ratio: 1:6.

PREPARATION of Delipidated Serum: Fetal calf serum (100 mL) and CAB-O-Sil (2 grams) stir overnight at 4° C. and centrifuge at 16,000 rpm for 5 hrs. Filter supernatant and store at 4° C.

48 hrs. prior to harvest, switch cells grown in MEM with Fetal Calf serum to MEM with 10% delipidated serum.

3. Harvest

Remove medium, wash with PBS, add fresh trypsin (0.25%)-EDTA (0.02%) with Hank's Balanced Salt solution, rinse and remove. Incubate flask at 37° C. until cells detach. Add 6 mL of MEM medium per flask to suspend cells and combine into centrifuge tube. Spin cells at 1,000 rpm for 5 mins. Wash by resuspending cell pellet in PBS and repeat centrifuging. Count cells ($2.5 \times 10^9$ yield from 18 flasks (75 cm$^2$). Resuspend in 10 mL of 50 mM HEPES (N-[2-Hydroxyethyl]piperazine-N'-[2-ethane-sulfonic acid]) containing 5 mM MgCl$_2$, 2 mM MnCl$_2$, 10 mM DTT, pH 7.5 (enzyme suspension buffer).

4. Cell Extracts

Sonicate (probe sonicator setting #60, pulse) the cell suspension on ice for 2 min. After a 1 min. cooling on ice, the sonication is repeated until greater than 90% of the cells are broken as observed microscopically. Centrifuge cell suspension for 10 mins. at 10,000 rpm. Transfer supernatant to clean tube and centrifuge at 20,000 rpm for 20 mins. The HepG2 enzyme preparation was centrifuged at 34,000 rpm to separate the cytosol and microsomal enzymes. The enzyme suspension was diluted 1 to 250 and used to perform the squalene synthetase assay using 3 μM $^3$H-farnesyl pyrophosphate as the substrate.

Squalene Synthase Assay

Reactions were performed in 1.2 mL polypropylene tube strips of 8. Buffer mixture and subtrate mixture for the assay were prepared from the following solution:

Buffer mixture contains 270 mM HEPES, pH 7.5, 20 mM Potassium fluoride and 5.4 mM Dithiothreitol(DTT). 55 μL of this mixture was used per assay. The final concentrations of HEPES, KF and DTT in the assay are 150 mM, 11 I mM and 3 mM respectively.

Substrate mixture:

| Stock concentration | μL used per assay | Final concentration |
|---|---|---|
| 1. MgCl$_2$, 55 mM | 10 | 5.5 mM |
| 2. NADPH, 10 mM (made fresh) | 10 | 1 mM |
| 3. Squalene Epoxidase inhibitor, Banyu FW-439H, 0.5 mg per mL | 0.02. | 0.1 μg per mL |
| 4. $^3$H-farnesyl-pyrophosphate, 25 μM, 20 Ci per mole | 0.24 | 0.06 μM |
| 5. Farnesyl-pyrophosphate, 3 mM | 0.098 | 2.94 μM |
| 6. Water | 9.63 | |

For each reaction, 55 μL of buffer mixture was taken with 5 μL of an inhibitor solution in DMSO and 10 μL of diluted enzyme (1 to 250 as described in the enzyme preparation; the final protein concentration of enzyme in the assay is 2 μg per mL.). The inhibitor solution was prepared by dissolving dry sample in DMSO. The reaction was initiated by the addition of 30 μL of substrate solution and the mixture was incubated at 30° C. for 20 minutes. The reactions were stopped by the addition of 100 μL of 95% EtOH, vortexed, and 100 μL of a suspension of 1 gmm per mL of Bio-Rad AG 1×8 resin (400 mesh, chloride form) was then added, vortexed. 300 μL of heptane was added to each tube strip and the strips were capped and vortexed for 10 minutes. 150 μL of heptane layer was then removed into a 96 deep well plate and mixed with 150 μL of scintillation fluid and the radioactivity was determined by liquid scintillation counting. The controls were run with 5 μL of DMSO and blanks were run with the addition of 100 μL of 95% EtOH to denature the enzyme before the addition of the substrate mixture to the assay tube.

$$\frac{(\text{Control} - \text{Sample}) \times 100}{\text{Control} - \text{Blank}}$$

IC$_{50}$ values were determined by plotting the log of the concentration of the test compound versus the percentage inhibition. The IC$_{50}$ is the concentration of inhibitor that give 50% inhibition as determined from these plots. The IC$_{50}$ of Composition A of this invention was found to be <2 μM.

The present compounds also demonstrate broad spectrum antifungal activity as determined by broth and agar dilution methods. The compounds are particularly active towards filamentous fungi and yeasts including *Candida albicans* and *Cryptococuss neoformans*. The sensitivity of filamentous fungi and yeast is determined using inhibitor dilution assays in microtiter format. The compounds are dissolved in DMSO at 2 mg/mL and serially diluted in 0.1 M phosphate buffer, pH 7.0 in the microtiter dish from 100 to 0.006 μg/mL. A standardized spore suspension for testing the filamentous fungi is prepared by inoculating Antibiotic Medium #3 containing 1.5% agar with spores such that $1.5 \times 10^3$ colony forming units were added per well. The microtiter wells are filled with 50 μL of buffer containing compound and 50 μL of inoculated medium.

The sensitivity of yeasts is determined by inoculating yeast nitrogen base containing 1% dextrose (YNB/G) with aliquots of an overnight yeast culture grown in Yeast Morphology (YM) media at 35° C. and diluting in YNB/G to yield a final concentration of $1.5-7.5 \times 10^3$ colony forming units/well. To test the sensitivity of yeast, compound is solubilized in 10 percent aqueous DMSO at 2.56 mg/mL. The compound is diluted serially in YNB/G from 128 to 0.06 μg/mL and further diluted 1:10 in YNB/G. The wells are filled with 150 μL of media containing drug. The minimum inhibitory concentration (MIC) is defined as the lowest concentration to prevent growth after an incubation for 42 hours, at 28° C. for the filamentous fungi and 24 to 48 hours, at 35° C. for the yeasts.

Thus the present invention is also directed to a method of treating fungus infections which comprises the administration to an organism in need of such treatment a nontoxic therapeutically effective amount of a compound represented by the structural formula (I) and pharmaceutically acceptable salts thereof. Generally from 2 to about 5 mg/kg should be employed as a unit dosage in an antifungal treatment.

The compounds of this invention are adaptable to being utilized in various applications of antifungal compositions. In such use, compounds may be admixed with a biologically inert carrier, generally with the aid of a surface active dispersing agent, the nature of which would vary depending on whether the use is for the control of pathogens infecting mammals such as man, or birds or reptiles, or for control of fungi in agriculture such as in soil or plant pans, or for the control of fungi in inanimate objects.

In compositions for medical applications, the compounds may be admixed with a pharmaceutically acceptable carrier, the nature of which will vary depending on whether the composition is to be topical, parenteral or oral.

If said application is to be topical, the drug may be formulated in conventional creams and ointments such as white petroleum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by intimately mixing the component drugs with any of the usual pharmaceutical media, including, for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricant such as calcium stearate, together with binders, disintegrating agents and the like.

These compositions are then administered in amounts sufficient to obtain the desired antifungal effect. For medical application, the method comprises administering to a subject in need of treatment a therapeutically effective antifungal amount of a compound of formula I. The appropriate doses will vary depending on age, severity, body weight and other conditions. For topical application the compositions are applied directly to the area where control is desired. For internal administration, the composition may be applied by injection or may be administered orally.

For non-medical application, the product of the present invention, either singly or as a mixture, may be employed in compositions in an inert-carrier which includes finely divided dry or liquid diluents, extenders, fillers, conditioners and excipients, including various clays, diatomaceous earth, talc, and the like, or water and various organic liquids such as lower alkanols, for example ethanol and isopropanol, or kerosene, benzene, toluene and other petroleum distillate fractions or mixtures thereof to inhibit fungal growth.

These compositions may be employed by applying to the surface of or incorporating in the medium to be protected. For the control of rice blast, tomato late blight, tomato early blight, wheat leaf rust, bean powdery mildew and tomato Fusarium wilt, the compositions may be applied directly to the plant in topical application or administered to the soil for systemic application. The method comprises administering to the affected plant, soil or medium to be protected an antifungally effective amount of the compound of formula I.

The following examples illustrate the preparation of the compounds of formula (I) and their incorporation into pharmaceutical compositions and, as such, are not to be considered as limiting the inventions set forth in the claims appended hereto.

EXAMPLE 1

A. Preparation of Compound A

A solution of 2.5 mg/mL of Zaragozic Acid A in dimethyl sulfoxide (DMSO) was prepared and 30 mL aliquots of this solution were placed in each of five 250 mL Erlenmeyer flasks. The samples were placed in a 37° C. incubator at a distance of 25–30 cm from a fluorescent light and were exposed to air. The reaction was allowed to continue for 6–8 days prior to isolation.

B. Isolation of Compound A

The five samples from Step A above were combined and diluted with three volumes of water and then applied to a large HP-20 colunto (bed volume about 800 mL). Most of the DMSO was removed in several liters of water washings. The chromatogram was developed in a stepwise gradient mode using a solvent mixture of water-methanol beginning with volume ratios of 100:0 (i.e., the aforementioned water washings), 90:10, 80:20, etc. in 10% increments up to 0:100. Fractions containing greater than 60% methanol contained the compound of interest; several liters were concentrated to about 20 mL and filtered for preparative HPLC. The final purification was done using a semiprep Beckman Ultrasphere ODS column (25cm×9.2mm ID) with a mobile phase gradient from 54 to 74% acetonitrile (plus water containing 0.1% phosphoric acid) over 30 minutes, with a 5 minute hold at 74% before returning to initial conditions. The flow rate was 4.0 mL/min. and UV detection was at 215 nm. The retention time of Compound A was 30.7 min. Phosphoric acid was removed by passage of the collected eluates through a C18 solid phase extraction cartridge.

$^1$H NMR (400 MHz) (CD$_3$OD): 7.25 (m, 2H), 7.16 (m, 1H), 7.15 (m, 2H), 6.89 (dd, 15.7, 8.5, 1H), 5.83 (dd, 15.7, 1.0, 1H), 5.53 (d, 2.4, 1H), 4.98 (d, 4.9, 1H), 4.94 (s, 1H), 4.90 (s, 1H), 4.64 (d, 2.4, 1H), 2.80 (m, 2H), 2.67 (dd, 13.4, 6.4, 1H), 2.43 (m, 1H), 2.42 (dd, 13.4, 8.5, 1H), 2.29 (m, 1H), 2.19 (m, 1H), 2.08 (s, 3H), 1.32 (m, 3H), 1.13 (m, 2H), 1.02 (d, 6.8, 3H), 0.85 (t, 7.2, 3H), 0.85 (d, 6.8, 6H).

Mass Spec (FAB): M-1=529.

EXAMPLE 2

As a specific embodiment of an oral composition of a compound of this invention, 20 mg of compound A from Example 1 is formulated with sufficient finely divided lactose to provide a total amount of 580 to 590 mg to fill a size 0 hard gelatin capsule.

EXAMPLE 3

Preparation of an Ammonium Salt

A 0.1 mmol sample of the free acid of a compound of formula (I) is dissolved in 10 mL of ethyl acetate. The resulting solution is saturated with gaseous ammonia upon which the ammonium salt precipitates from solution.

EXAMPLE 4

Preparation of a Potassium Salt

A solution of 0.1 mmol of the free acid of a compound of formula (I) in 10 mL of methanol is treated with an aqueous or methanolic solution containing 0.1 mmol of potassium hydroxide. Evaporation of the solvent affords the potassium salt.

In a similar fashion the sodium and lithium salts can be formed.

EXAMPLE 5

Preparation of a Calcium Salt

A solution of 0.1 mmol of the free acid of a compound of formula (I) in 20 mL of 6:4 methanol/water is treated with an aqueous solution of 0.1 mmol of calcium hydroxide. The solvents are evaporated to give the corresponding calcium salt.

EXAMPLE 6

Preparation of an Ethylenediamine Salt

A solution of 0.1 mmol of the free acid of a compound of formula (I) in 10 mL of methanol is treated with 0.1 mmol of ethylenediamine. Evaporation of the solvent affords the ethylenediamine salt.

The procedure can also be applied to the preparation of the N,N''-dibenzylethylenediamine salt.

EXAMPLE 7

Preparation of a Tris(hydroxymethyl)aminomethane Salt

To a solution of 0.1 mmol of the free acid of a compound of formula (I) in 10 mL of methanol is added from 0.1 mmol of tris(hydroxymethyl)aminomethane dissolved in 10 mL of methanol. Evaporation of the solvent gives the tris(hydroxymethyl)aminomethane salt. Similarly prepared are the salts of L-ornithine, L-lysine, and N-methylgluacamine.

EXAMPLE 8

Preparation of an L-arginine Salt

A solution of 0.1 mmol of the free acid of a compound of formula (I) in 10 mL of 6:4 methanol/water is treated with an aqueous solution of 0.1 mmol of L-arginine. Evaporation of the solvent affords the L-arginine salt.

Similarly prepared are the salts of L-omithine, L-lysine and N-methylglucamine.

EXAMPLE 9

Preparation of a Compound C (Method 1)

A solution of 2 mg of Compound A in 5 mL of methanol/ether (1:1) is treated with a slight excess of ethereal diazomethane. After 5 minutes, excess diazomethane is removed and the solvent is evaporated to give Compound C.

EXAMPLE 10

Preparation of Compound C (Method 2)

A solution of 2 mg of Compound A in 0.5 mL of acetonitrile is treated at room temperature with 10 equivalents of DBU and 10 equivalents of methyl iodide. After 2 hours, the reaction is diluted with 10 mL of dichloromethane and washed successively with 10 mL of 0.1 M phosphoric acid, 10 mL of water, 10 mL of saturated sodium bicarbonate and 10 mL of water. After drying over sodium sulfate, the organic layer is concentrated and the residue is chromatographed on silica gel using mixtures of hexane and ethyl acetate to give Compound C.

The method of Example 10 is also suitable for the preparation of other ester derivatives such as 1) ethyl and other lower alkyl esters; and 2) benzyl and substituted esters.

EXAMPLE 1

Preparation of the pivalate ester Compound B

To a solution of 2 mg of Compound A in 0.5 mL of refluxing acetonitrile is added 10 equivalents of DBU followed by 10 equivalents of chloromethyl pivalate and a few crystals of sodium iodide. The reaction is stirred overnight, then concentrated in vacuo. The residue is purified by preparative HPLC, using a C-8 reverse phase column and a gradient solvent of water-acetonitrile to give Compound B.

What is claimed is:

1. A compound of structural formula (I)

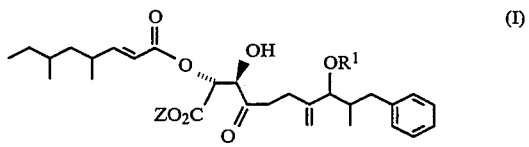

wherein
$R^1$ is selected from the group consisting of hydrogen and acetyl; and
Z is selected from the group consisting of
  (a) hydrogen;
  (b) $C_{1-5}$alkyl;
  (c) $C_{1-5}$alkyl substituted with a member of the group consisting of
    (i) phenyl
    (ii) phenyl substitute with methyl, methoxy, halogen, (Cl, Br, I, F) or hydroxy; and
    (iii) $C_{1-5}$alkylcarbonyloxy;
  (d) —$CH_2$—CH=$CH_2$;

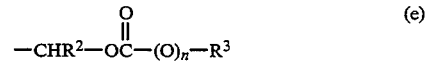

wherein
$R^2$ is —H or $C_{1-4}$alkyl,
n is zero or 1, and
$R^3$
  (a) $C_{1-5}$ alkyl,
  (b) phenyl, or
  (c) phenyl substituted with X and Y, defined below,

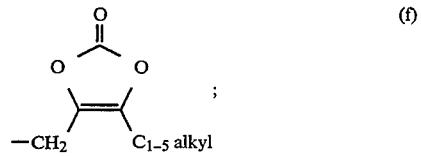

and

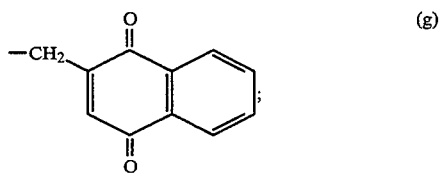

and

X and Y are each independently selected from:
  (1) hydrogen, (2) hydroxy,
(3) halogen,
(4) trifluoromethyl,
(5) $C_{1-4}$ alkyl,
(6) $C_{1-4}$ alkyl—O—
(7) $C_{1-4}$ alkyl—C(O)—O—
(8) $CO_2C_{1-4}$ alkyl,
(9) —$CO_2H$, and
(10) nitro;

or a pharmaceutically acceptable salt thereof.

2. A compound of claim 1 wherein $R^1$ is acetyl or a pharmaceutically acceptable salt thereof.

3. A compound of claim 2, wherein Z is selected from the group consisting of
   (a) Hydrogen;
   (b) $C_{1-5}$ alkyl; and
   (c) $C_{1-5}$ alkyl substituted with $C_{1-5}$ alkylcarbonyloxy;
or a pharmaceutically acceptable salt thereof.

4. A compound of claim 3, wherein Z is hydrogen or a pharmaceutically acceptable salt thereof.

5. A pharmaceutical composition comprising a nontoxic therapeutically effective amount of a Compound of claim 1 and a pharmaceutically acceptable carrier.

6. A pharmaceutical composition comprising a nontoxic therapeutically effective mount of a compound of claim 1 in combination with a pharmaceutically acceptable nontoxic cationic polymer capable of binding bile acids in a non-reabsorbable form in the gastrointestinal tract and a pharmaceutically acceptable carrier.

7. A method of treating hypercholesterolemia comprising the administration to a subject in need of such treatment a nontoxic therapeutically effective amount of a compound of claim 1.

8. A method of inhibiting squalene synthase comprising the administration to a subject in need of such treatment a nontoxic therapeutically effective mount of a compound of claim 1.

* * * * *